US00PP27252P3

(12) United States Plant Patent
Helvick et al.

(10) Patent No.: US PP27,252 P3
(45) Date of Patent: Oct. 11, 2016

(54) ***LANTANA* PLANT NAMED 'PIIL-I'**

(50) Latin Name: ***Lantana camara* L.**
Varietal Denomination: PIIL-I

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 175 days.

(21) Appl. No.: 14/121,507

(22) Filed: Sep. 12, 2014

(65) Prior Publication Data

US 2016/0081246 P1 Mar. 17, 2016

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Keith Robinson
(74) *Attorney, Agent, or Firm* — Lathrop & Gage LLP

(57) ABSTRACT

A new and distinct cultivar of *Lantana* plant named 'PIIL-I', characterized by its low growing, layered and spreading growth habit; leathery, scabrous, lustrous dark green foliage; continuous flowering; and dark yellow flower buds that open to dark yellow and age to orange and eventually to orange-red. There are no other cultivars of *Lantana* with this combination of characteristics known to the inventor.

2 Drawing Sheets

Genus and species of plant claimed: *Lantana camara* L.
Variety denomination: 'PIIL-I'.

BACKGROUND OF THE INVENTION

The present invention relates to a new and distinct cultivar of *Lantana* plant, botanically known as *Lantana camara*, and hereinafter referred to by the cultivar name 'PIIL-I'.

The new *Lantana* plant originated from a controlled cross between *Lantana camara* 'Dallas Red' (not patented), female parent, and *Lantana camara* 'Sunset Orange' (U.S. Plant Pat. No. 24,120), male parent, as part of a planned breeding program to develop low growing, continuously flowering *lantanas* with dark green foliage. The cultivar 'PIIL-I' originated and was discovered in a cultivated environment in Watkinsville, Ga.

Asexual reproduction of the new cultivar by stem cuttings in Watkinsville, Ga. has shown that all the unique features of this new *Lantana*, as herein described, are stable and reproduced true-to-type through successive generations of such asexual propagation.

SUMMARY OF THE INVENTION

Plants of the new cultivar 'PIIL-I' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIL-I'. These characteristics in combination distinguish 'PIIL-I' as a new and distinct cultivar: 1. Low growing, layered and spreading growth habit; 2. Leathery, scabrous, lustrous dark green, fragrant foliage; 3. Continuous flowering; and 4. Dark yellow flower buds that open to dark yellow, age to orange and then eventually to orange-red. There are no other cultivars of *Lantana* with this combination of characteristics known to the inventor.

Plants of the new *Lantana camara* 'PIIL-I' differ from plants of the male parent, 'Sunset Orange', (U.S. Plant Pat. No. 24,120) primarily in flower color, as plants of 'Sunset Orange', (U.S. Plant Pat. No. 24,120) have light orange flower buds that open to light orange and age to dark orange, whereas plants of 'PIIL-I' have buds that open to dark yellow and age to orange eventually to orange-red. Plants of the new *Lantana camara* 'PIIL-I' are more spreading in habit compared to the stiff, bushy, habit of *Lantana camara* 'Sunset Orange'.

Plants of the new *Lantana* can be compared to plants of *Lantana camara* 'Dallas Red' (unpatented), the female parent, mainly in flower color. 'PIIL-I' starts off as dark yellow turns to orange and ages to orange-red, whereas plants of *Lantana camara* 'Dallas Red' (unpatented) start off red turn to orange and yellow with aging.

Plants of the new *Lantana* 'PIIL-I' can be compared to plants of *Lantana* sp. 'Chapel Hill Gold' (U.S. Plant Pat. No. 21,539) primarily in flower color and cold hardiness. Plants of 'PIIL-I' flowers start off dark yellow and turn to orange and then age to orange-red, whereas plants of *Lantana* 'Chapel Hill Gold' start off bright yellow gold and remain that color. Plants of 'Chapel Hill Gold' are cold hardy in USDA zone 7. Plants of 'PIIL-I' are not cold hardy. In zone 7 they are annuals.

BRIEF DESCRIPTION OF THE DRAWINGS

The accompanying color photographs illustrate the flower and foliage characteristics and the overall appearance of the new *Lantana*, showing the colors as true as it is reasonably possible to obtain in color reproductions of this type. Colors in the photographs may differ slightly from the color values cited in the detailed botanical description which accurately describe the colors of the new *Lantana*.

DETAILED DESCRIPTION

Figure 1:
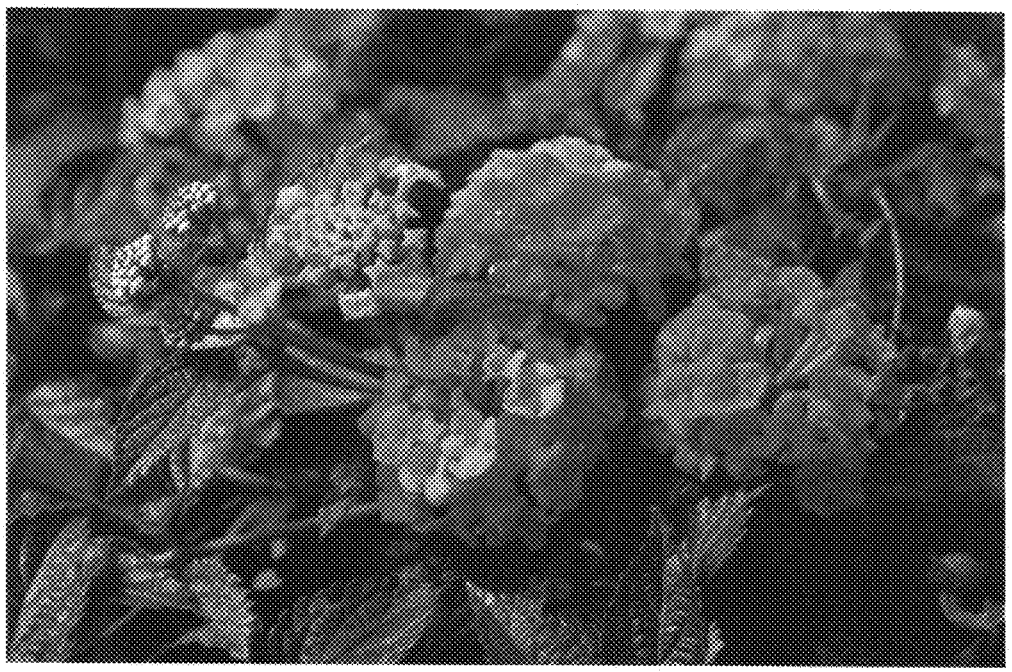
FIG. 1 illustrates a close-up view of the inflorescences and foliage of a two-year-old 'PIIL-I' plant.
Figure 2:
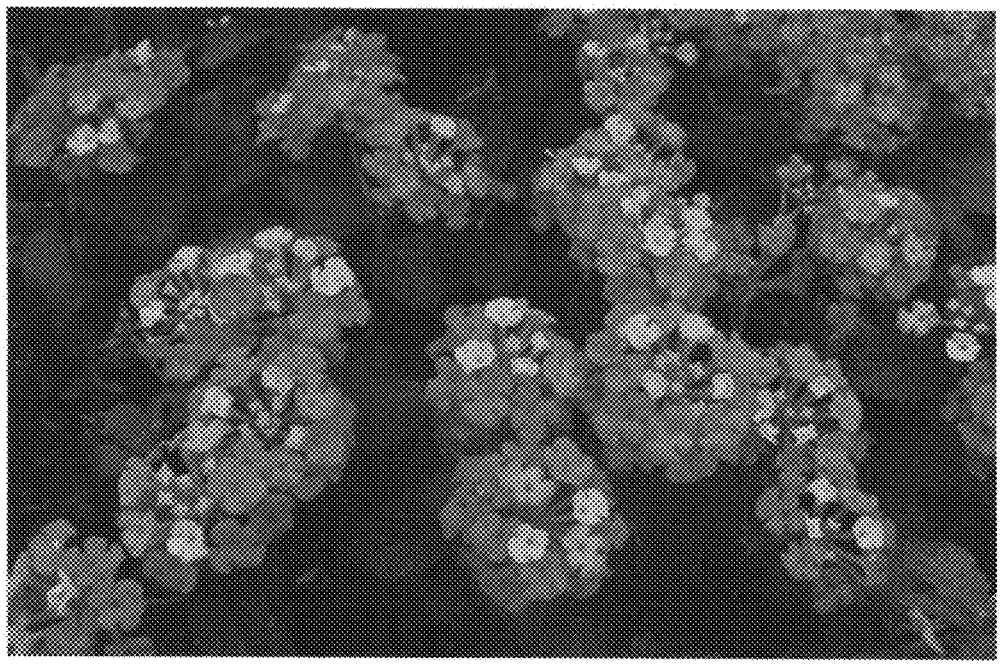
FIG. 2 illustrates the overall appearance of a two-year-old 'PIIL-I' plant in a 11.8 L container.

In the following description, color references are made to The Royal Horticultural Society Colour Chart, 2007 Edition, except where general terms of ordinary dictionary significance are used. Plants used for the description were approximately two-years-old and were grown in 11.8 L containers in full sun under outdoor conditions in a nursery in Watkinsville, Ga.

Botanical classification: *Lantana camara* 'PIIL-I'.

Parentage: Female or seed parent: *Lantana camara* 'Dallas Red' (not patented). Male or pollen parent: *Lantana camara* 'Sunset Orange' (U.S. Plant Pat. No. 24,120) (controlled-pollination).

Propagation: Stem cuttings.

Time to initiate roots, summer: About 10 days at 32° C.

Time to produce a rooted young plant, summer about 4 months at 32°.

Plant description: Herbaceous flowering plant, subshrub, low growing, layered and spreading growth habit. Freely branching habit with about three to four primary lateral branches per plant; each primary lateral branch with potentially two secondary lateral branches developing at each node. Pinching enhances lateral branch development. Length about 37.5 cm.

- *Root description.*—Numerous, fine, fibrous and well-branched.
- *Plant size.*—About 24 cm in height from the media level to the top of the inflorescences, and about 75 cm in diameter.
- *Plant vigor.*—Medium. Young stems have a diameter of about 3 mm and a squarish shape. Mature stems have a diameter of about 4 mm or more and a rounded shape. Quantity of main branches per plant 3-4. Length of stems about 37.5 cm.
- *Stem strength.*—Strong, but flexible.
- *Stem texture.*—Coarse, pubescent.
- *Stem color* (*young*).—144A. Color (mature): 199C.
- *Internode length.*—About 3 cm.

Vegetative buds: Opposite in arrangement, valvate, ovoid, pubescent.

- *Color.*—144A.
- *Size.*—About 1 mm in length and about 1 mm in width.

Foliage description:

- *Arrangement.*—Opposite, simple.
- *Length.*—About 3.5 cm.
- *Width.*—About 2 cm.
- *Shape.*—Ovate.
- *Apex.*—Acute.
- *Base.*—Cuneate.
- *Margin.*—Dentate.
- *Texture* (*upper surface*).—Leathery, moderately waxy, with scabrous pubescence.
- *Texture* (*lower surface*).—Rough, with hispid pubescence.
- *Venation pattern.*—Pinnate.
- *Venation color* (*upper surface*).—144B.
- *Venation Color*(*lower surface*).—144B.
- *Fragrance.*—Pungent, mint-like.
- *Color of developing foliage* (*upper surface*).—146B.
- *Color of developing foliage* (*lower surface*).—147B.
- *Color of mature foliage* (*upper surface*).—147A.
- *Color of mature* (*lower surface*).—147B.
- *Petiole length.*—About 5 mm.
- *Petiole diameter.*—About 2 mm.
- *Petiole texture, both surfaces.*—Hispid pubescence.
- *Petiole color* (*upper and lower surfaces*).—144A.
- *Quantity of leaves.*—There are about 25 leaves per branch.
- *Leaf aspect.*—The leaf apex is at a 45° angle from the branch.

Flower description:

- *Flower type and habit.*—Small salverform flowers arranged in axillary corymbs; flowers face mostly upward or outward. Flowers are self-cleaning. Freely flowering with potentially two inflorescences per node; typically about 22 to 28 flowers per corymb.
- *Natural flowering season.*—Spring until the first frost in fall; flowering is continuous.
- *Flower longevity on the plant.*—About one week.
- *Fragrance.*—None observed.
- *Inflorescence diameter.*—About 4 cm.
- *Inflorescence height.*—About 2.5 cm.
- *Flower bud length.*—About 1 cm.
- *Flower bud diameter.*—About 3 mm.
- *Flower bud Shape.*—Oblong.
- *Flower bud color.*—N30A.
- *Flower appearance.*—Flared trumpet, corolla fused, four-parted; flowers roughly rectangular in shape.
- *Diameter.*—About 1 cm.
- *Corolla tube length.*—About 1 cm.
- *Depth* (*height*).—About 1.5 cm.
- *Throat diameter.*—About 1.5 mm.
- *Tube length.*—About 1.1 cm.
- *Pedicels.*—None observed, flowers not stalked, sessile.

Petals:

- *Arrangement/appearance.*—Single whorl of four petals, fused into flared trumpet.
- *Diameter.*—About 9 mm by 11 mm.
- *Depth* (*height*).—About 1.5 cm.
- *Throat diameter.*—About 1 mm.
- *Tube length.*—About 1.1 cm.
- *Petal length from throat.*—About 5 mm for the upper petal, about 4 mm for the lower petal, and about 4 mm for the lateral petals.
- *Petal width.*—About 6 mm for the upper petal, about 5 mm for the lower petal, and about 4 mm for the lateral petals.
- *Petal shape.*—Spatulate to somewhat orbicular.
- *Petal apex.*—Obtuse.
- *Petal base.*—Fused.
- *Petal margin.*—Entire.
- *Petal texture, upper and lower surfaces.*—Smooth, glabrous.
- *Petal color* (*young*).—Upper surface: 14A and lower surface: 14A.
- *Color of throat.*—14A.
- *Color of corolla tube.*—14A.
- *Petal color* (*mature*).—Upper and lower surfaces, throat, and corolla tube: N25A.
- *Petal color* (*aged*).—Upper and lower surfaces, throat, and corolla tube: N30A.

Sepals:

*Arrangement/appearance.*—One sepal per flower at the base of the corolla, leaf-like. Length is about 6 mm. Width is about 2 mm.

*Shape.*—Lanceolate.

*Apex.*—Acute.

*Margin.*—Entire.

*Texture, upper and lower surface.*—Scabrous.

*Sepal color, upper and lower surfaces.*—146A.

Peduncles:

*Length.*—About 2 cm.

*Diameter.*—About 1.5 mm.

*Angle.*—About 45 degrees from the stem.

*Texture.*—Pubescent.

*Strength.*—Flexible, but strong.

*Color.*—144A.

Stamens:

*Quantity/arrangement.*—Four per flower, adnate to the inside of the corolla tube.

*Anther shape.*—Oblong.

*Anther length.*—1 mm.

*Anther width.*—Less than 1 mm.

*Anther color.*—13B.

*Filament length.*—1 mm.

*Filament color.*—155D.

*Pollen amount.*—Produced in very small quantities, and 13B in color.

Pistils:

*Quantity.*—One inferior pistil per flower.

*Pistil length.*—About 3.5 mm.

*Pistil color.*—145C.

*Stigma shape.*—Rounded.

*Stigma size.*—About 1 mm in diameter.

*Stigma length.*—Less than 1 mm.

*Stigma color.*—145C.

*Style length.*—About 1.5 mm.

*Style color.*—145C.

*Ovary size.*—About 1 mm in diameter.

*Ovary color.*—145A.

Fruit:

*Type/appearance.*—Drupe.

*Shape.*—Round.

*Diameter.*—About 5 mm.

*Texture.*—Smooth.

*Mature color.*—202A.

*Number per infructescence.*—Ranges from zero to about five.

Seed:

*Amount produced.*—One seed per fruit.

*Size.*—Diameter about 2.5 mm.

*Texture.*—Smooth.

*Color.*—199D.

Disease/pest resistance: Plants of the claimed *Lantana* cultivar grown in the garden have not been noted to be susceptible or resistant to pathogens and pests common to *Lantana*.

We claim:

1. A new and distinct *Lantana* plant named 'PIIL-I', as illustrated and described herein.

* * * * *